United States Patent [19]

Cianci

[11] 4,264,312
[45] Apr. 28, 1981

[54] BODY CHANNEL SIMULATION DEVICE
[75] Inventor: James P. Cianci, Cary, Ill.
[73] Assignee: The Kendall Company, Boston, Mass.
[21] Appl. No.: 143,990
[22] Filed: Apr. 28, 1980
[51] Int. Cl.³ ............................................. G09B 23/28
[52] U.S. Cl. ................................................... 434/262
[58] Field of Search .................................. 35/17, 19 R
[56] References Cited

U.S. PATENT DOCUMENTS

| 3,208,161 | 9/1965 | Balinkin | 35/19 R |
| 3,209,469 | 10/1965 | James | 35/17 |
| 3,426,449 | 2/1969 | Van Noy, Jr. | 35/17 |
| 3,766,666 | 10/1973 | Stroop | 35/17 |
| 4,140,127 | 2/1979 | Cianci . | |
| 4,178,735 | 12/1979 | Jackson . | |

Primary Examiner—Harland S. Skogquist
Attorney, Agent, or Firm—Powell L. Sprunger

[57] ABSTRACT

A device for simulating catheterization in a body channel of a patient comprising, a catheter having an elongated shaft, an inflation balloon on the shaft, and an inflation lumen extending along the shaft and communicating with the balloon. The device has a sleeve of flexible material defining a cavity to receive the portion of the shaft containing the balloon, with the sleeve having a sufficiently small width such that the balloon contacts walls of the sleeve when inflated. The sleeve has a line of weakness which ruptures when the balloon is sufficiently inflated unless relieved of pressure prior to rupture of the sleeve.

5 Claims, 3 Drawing Figures

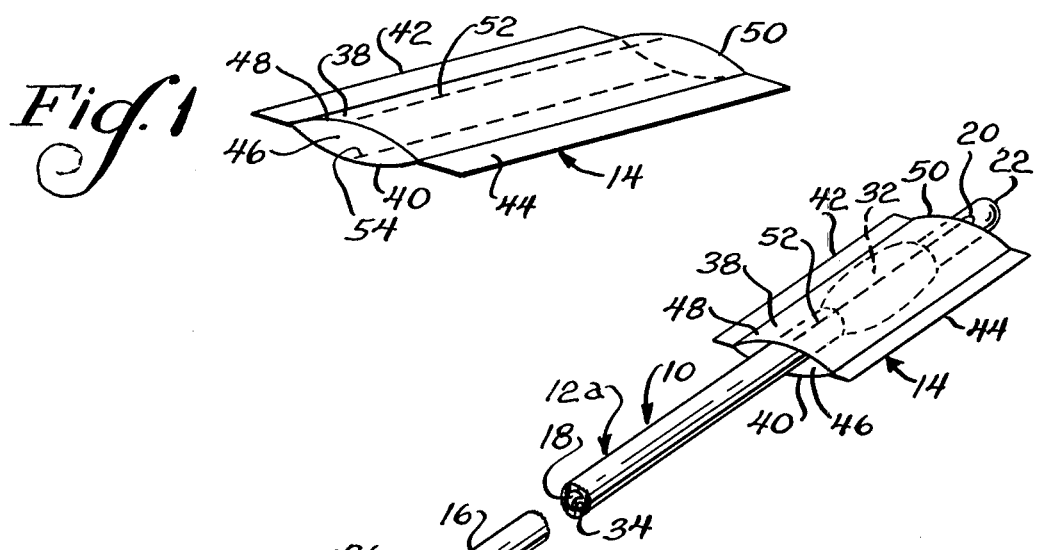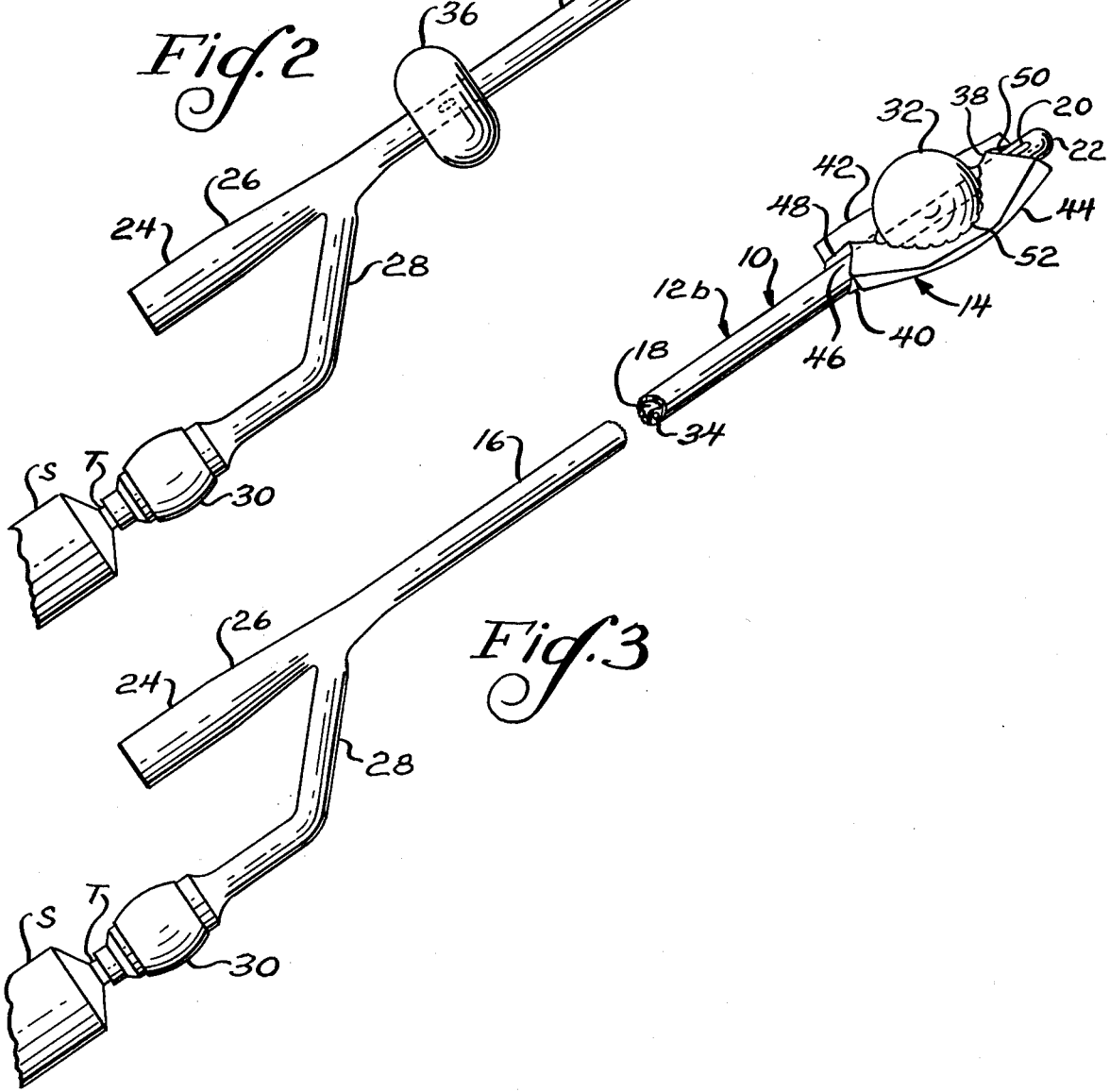

BODY CHANNEL SIMULATION DEVICE

BACKGROUND OF THE INVENTION

The present invention relates to catheters, and more particularly to catheter simulation devices.

A various assortment of catheters of the Foley type have been proposed for use in catheterizing a patient. Such Foley catheters have an elongated shaft defining a drainage lumen and a drainage eye adjacent a distal end of the shaft, an inflatable balloon adjacent the distal end of the shaft, and an inflation lumen extending along the shaft and communicating with the balloon. When properly used, the catheter shaft is passed through the urethra until the drainage eye and balloon are located in the bladder, and the balloon is inflated in the bladder to retain the catheter in place. During catheterization, urine drains through the drainage eye and lumen of the catheter to a collection bag connected to the catheter for collection therein.

However, in the event that the catheter shaft has not been passed a sufficient distance through the urethra, unknown to the physician, the balloon may be located in the urethra when inflated. As a result, the inflated balloon may rupture the patient's urethra causing serious harm to the patient. The U.S. Pat. Nos. 3,543,758 and 3,543,759, incorporated herein by reference, disclose catheters having a safety balloon communicating with the inflation lumen, such that the safety balloon inflates when the retention balloon is impeded by the urethra during inflation to relieve pressure in the retention balloon. Thus, the safety balloon prevents overinflation of the retention balloon when impeded by the urethra, such that the safety balloon prevents possible harm to the patient if the catheter has been improperly positioned with the balloon in the urethra.

SUMMARY OF THE INVENTION

A feature of the invention is the provision of a device for simulating catheterization in the urethra of a patient.

The device of the present invention comprises, a catheter having an elongated shaft, an inflatable balloon on the shaft, and an inflation lumen extending along the shaft and communicating with the balloon. The device has a sleeve of flexible material defining a cavity to receive the portion of the shaft containing said balloon. The sleeve has a width slightly larger than the uninflated balloon, and a line of weakness in a wall of the sleeve.

A feature of the invention is that the balloon contacts the walls of the sleeve when the balloon is inflated.

Another feature of the invention is that the balloon of a conventional Foley catheter ruptures the line of weakness when the balloon is sufficiently inflated.

Yet another feature of the invention is that the safety balloon in a catheter of the type disclosed in U.S. Pat. Nos. 3,543,758 and 3,543,759 is actuated without rupture of the line of weakness when the retention balloon is sufficiently inflated.

Thus, a feature of the invention is that the device simulates catheterization in the patient's urethra when used in connection with a conventional Foley catheter and a catheter having a safety balloon.

Further features will become more fully apparent in the following description of the embodiments of this invention and from the appended claims.

DESCRIPTION OF THE DRAWINGS

In the drawings:

FIG. 1 is a perspective view of a sleeve for a device which simulates the urethra of a patient according to the present invention;

FIG. 2 is a fragmentary perspective view illustrating a catheter having a safety balloon when utilized with the sleeve of FIG. 1; and FIG. 3 is a fragmentary perspective view of a conventional Foley catheter when utilized with the sleeve of FIG. 1.

DESCRIPTION OF THE PREFERRED EMBODIMENTS

Referring now to FIGS. 2 and 3, there is shown a device generally designated 10 for simulating the urethra of a patient comprising a catheter 12a or 12b and a sleeve 14. With reference to FIG. 3, a conventional Foley catheter 12b is shown having an elongated shaft 16, a drainage lumen 18 extending through the shaft 16, and a drainage eye 20 adjacent a distal end 22 of the catheter 12b, with the drainage eye 20 communicating with the drainage lumen 18. The catheter 12b has a connector 24 adjacent a proximal end 26 of the catheter 12b, and a side arm 28 extending outwardly from the shaft 16 adjacent the proximal end 26 of the catheter 12b, with the side arm 28 having valve means 30 of known type at the outer end of the side arm 28. The catheter 12b has an inflatable retention balloon 32 of elastic material adjacent the distal end 22 of the catheter 12b, and an inflation lumen 34 extending through the side arm 28 and the shaft 16, such that the inflation lumen 34 communicates between the valve means 30 and the balloon 32.

In use, the catheter shaft 16 is passed through the patient's urethra with the balloon 32 in an uninflated configuration until the drainage eye 20 and balloon 32 are located in the patient's bladder. Next, the tip T of a syringe S is placed in the valve means 30 in order to actuate the valve means 30 and permit passage of fluid through the valve means 30. The syringe S is then pumped in order to eject fluid through the valve means 30 and inflation lumen 34 into the balloon 32 to inflate the balloon 32 in the patient's bladder, such that the inflated balloon 32 retains the catheter in place. A drainage tube (not shown) connected to a collection bag (not shown) is then attached to the connector 24 of the catheter 12b, such that during catheterization urine drains through the drainage eye 20, the drainage lumen 18, and the drainage tube to the collection bag for retention therein. However, if the catheter has been improperly positioned during the placement procedure, the uninflated balloon 32 may be located in the urethra of the patient. Hence, the balloon 32 may be inflated inside the urethra while the physician actually believes that the balloon is in the patient's bladder. As a result, the inflated balloon may rupture the urethra causing serious harm to the patient.

A catheter 12a of a type disclosed in U.S. Pat. No. 3,543,759 (or U.S. Pat. No. 3,543,758) is illustrated in FIG. 2. In this embodiment, the catheter 12a has a safety balloon 36 connected to the shaft 16 at a location such that the safety balloon 36 is located outside the patient's body when the retention balloon 32 is properly positioned in the patient's bladder. In the event that the retention balloon 32 is properly positioned in the patient's bladder, the safety balloon 36 remains uninflated when the retention balloon 32 is inflated in the bladder. However, in the event that the retention balloon 32 is improperly positioned in the urethra during inflation, the safety balloon 36 inflates when the retention balloon 32 contacts the walls of the urethra during inflation, such that the safety balloon 36 relieves pressure from the retention balloon 32 in order to prevent full inflation of the balloon 32 and prevent possible harm to the patient's urethra from the partially inflated balloon. Thus, the catheter 12a of FIG. 2 prevents harm to the patient in the event that the retention balloon 32 is erroneously inflated inside the patient's urethra.

With reference to FIG. 1, the sleeve 14 has a pair of opposed walls 38 and 40 of rectangular configuration, with the walls being sealed together adjacent their sides 42 and 44, such that the walls 38 and 40 define an elongated tunnel or cavity 46 extending between opposed longitudinal open ends 48 and 50 of the sleeve 14. As shown, the walls 38 and 40 have respective lines of weakness 52 and 54, such as lines of perforation, extending between the opposed ends 48 and 50 at a location intermediate the sides 42 and 44. With reference to FIGS. 1–3, the sleeve 14 has a length slightly longer than the length of the inflation balloon 32 of the catheters 12a and 12b, and the walls 38 and 40 of the sleeve 14 define the tunnel 46 with a width slightly larger than the diameter of the catheter shaft 16 and uninflated balloon 32, such that the balloon 32 contacts the walls 38 and 40 of the sleeve 14 when the balloon 32 is slightly inflated. The sleeve 14 may be constructed from any suitable flexible material, such as high density polyethylene.

With reference to FIG. 2, during demonstration of the effects of a catheter within the urethra, the balloon 32 of the safety catheter 12a is placed within the tunnel 46 of the sleeve 14 with the balloon 32 in an uninflated configuration. Next, the syringe S is placed in the valve means 30, and the syringe S is pumped in order to inflate the retention balloon 32 within the sleeve 14. When the retention balloon 32 is partially inflated such that the balloon 32 contacts the walls 38 and 40 of the sleeve 14, the safety balloon 36 is actuated and inflates to relieve pressure in the retention balloon 32 within the sleeve 14. This configuration of the catheter 12a is illustrated in FIG. 2. Thus, the safety balloon 36 inflates prior to rupture of the weakness lines 52 or 54 by the retention balloon 32, and the device 10 simulates the urethra of a patient where the tunnel 46 of the sleeve 14 serves as the lumen of the urethra while the walls 38 and 40 of the sleeve 14 serve as the walls of the urethra. Thus, the device 10 simulates the conditions in the urethra where the urethra or sleeve 14 remains in an intact configuration without rupture when the balloon 32 is inflated within the urethra or sleeve due to actuation of the safety balloon 36.

With reference to FIG. 3, during demonstration of the effects upon the urethra, the balloon 32 of the conventional Foley catheter 12b is placed within the sleeve 14 in an uninflated configuration. Next, the balloon 32 is inflated through use of the syringe S, and, since the balloon 32 inflates without a safety balloon to relieve pressure in the balloon 32, the inflated balloon 32 ruptures at least one of the weakness lines 52 or 54. This configuration is illustrated in FIG. 3. Thus, again the device 10 simulates the conditions within the urethra during balloon inflation where one wall 38 or 40 of the sleeve, which simulates the walls of the urethra, rupture during inflation of the balloon 32. In this manner, the effects of balloon inflation within the urethra for both the catheter 12a of FIG. 2 and the catheter 12b of FIG. 3 may be demonstrated through use of the sleeve 14 which remains in an intact configuration for the safety catheter 12a of FIG. 2 and which ruptures during inflation for the catheter 12b of FIG. 3.

The foregoing detailed description is given for clearness of understanding only, and no unnecessary limitations should be understood therefrom, as modifications will be obvious to those skilled in the art. For example, although described in connection with urinary catheters, a sleeve of suitable size may be used with catheters of a different type, such as endotracheal tubes.

I claim:

1. A device for simulating catheterization in a body channel of a patient, comprising:
   a catheter having an elongated shaft, an inflatable balloon on the shaft, and an inflation lumen extending along the shaft and communicating with said balloon; and
   a sleeve of flexible material defining a cavity to receive the portion of the shaft containing said balloon, said sleeve having a sufficiently small width such that the balloon contacts walls of the sleeve when inflated, said sleeve having a line of weakness which ruptures when the balloon is sufficiently inflated unless relieved of pressure prior to rupture of the sleeve.

2. The device of claim 1 wherein the sleeve has a pair of open ends, and in which the line of weakness comprises a perforation line extending between the ends of the sleeve.

3. The device of claim 1 wherein the sleeve has a pair of opposed walls, and a line of weakness in both of said walls.

4. A device for simulating catheterization in a body channel of a patient, comprising:
   a catheter having an elongated shaft, an inflatable balloon on the shaft, and an inflation lumen extending along the shaft and communicating with said balloon; and
   a sleeve of flexible material having a pair of opposed walls defining a pair of opposed open ends with the walls defining a tunnel extending through the sleeve between said ends, said sleeve having a length slightly longer than said balloon, said tunnel having a width slightly larger than the balloon when uninflated such that the balloon contacts the walls of the sleeve when inflated, at least one wall of the sleeve having a line of weakness extending between the ends of the sleeve such that the line of weakness ruptures when the balloon is sufficiently inflated into contact with the walls unless the balloon is relieved of pressure prior to rupture of the sleeve.

5. The device of claim 4 wherein both of said walls have a line of weakness extending between the ends of the sleeve.

* * * * *